United States Patent [19]
Nakamura et al.

[11] 4,321,411
[45] Mar. 23, 1982

[54] PROCESS FOR PRODUCING N-SUBSTITUTED ACRYLAMIDE OR METHACRYLAMIDE

[75] Inventors: Tomio Nakamura, Ichikawa; Shunichi Doi, Yokohama, both of Japan

[73] Assignee: Nitto Chemical Industry Co., Ltd., Tokyo, Japan

[21] Appl. No.: 243,112

[22] Filed: Mar. 12, 1981

[30] Foreign Application Priority Data

Mar. 12, 1980 [JP] Japan .................. 55-30276

[51] Int. Cl.$^3$ .......................................... C07C 102/06
[52] U.S. Cl. .................................................. 564/135
[58] Field of Search ........................................ 564/135

[56] References Cited

U.S. PATENT DOCUMENTS

| 3,288,794 | 11/1966 | Kuceski | 564/135 |
| 3,334,083 | 8/1969 | Beyerman et al. | 564/135 |
| 4,022,831 | 5/1977 | Spoerke | 564/135 |
| 4,206,143 | 6/1980 | Wenzel et al. | 564/135 |
| 4,256,666 | 3/1981 | McEntire | 564/135 |
| 4,258,200 | 3/1981 | Daughenbaugh | 564/135 |

Primary Examiner—Arthur P. Demers
Attorney, Agent, or Firm—Sughrue, Mion, Zinn, Macpeak and Seas

[57] ABSTRACT

A process is described for producing N-substituted acrylamide or methacrylamide comprising reacting an acrylic or methacrylic acid ester with an aliphatic or aromatic amine in liquid medium in the presence of a catalytic amount of alkyltin alkoxide.

11 Claims, 1 Drawing Figure

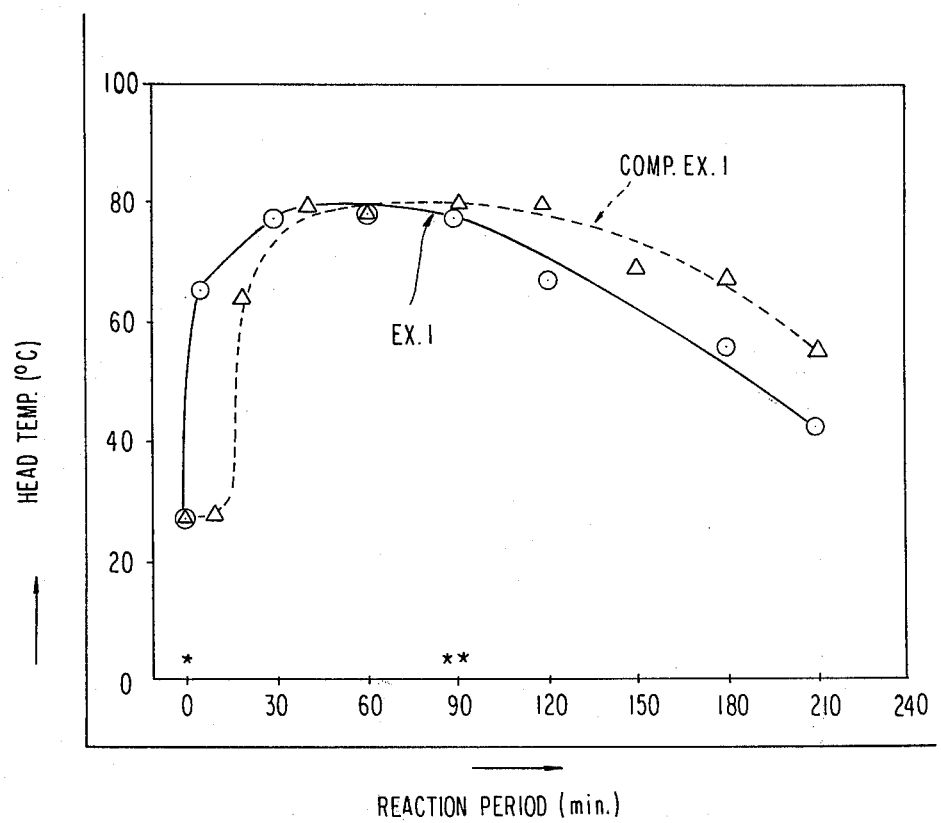

4,321,411

PROCESS FOR PRODUCING N-SUBSTITUTED ACRYLAMIDE OR METHACRYLAMIDE

FIELD OF THE INVENTION

This invention relates to a process for producing N-substituted acrylamide or methacrylamide, and more particularly, to a process for producing N-substituted acrylamide or methacrylamide by reacting an acrylic or methacrylic acid ester with an amine in liquid medium in the presence of an alkyltin alkoxide as catalyst.

BACKGROUND OF THE INVENTION

An N-substituted acrylamide or methacrylamide is a useful starting material for flocculants, textile, ion exchange resins, coatings, water-soluble films, photographic emulsions, etc. It is conventionally produced by reacting an acrylic or methacrylic acid ester with amine. More specifically, an acrylic or methacrylic acid ester can be reacted with at least 2 mols of tertiary amino alkylamine at a temperature between 20° C. and 200° C., whereupon aminolysis of the ester group and Michael addition to the carbon-carbon double bond take place simultaneously to produce the corresponding beta-aminopropionamide as an intermediate, which is then decomposed at a temperature between 180° C. and 300° C. to eliminate the amine attached to the carbon-carbon double bond so as to give N-(tertiary aminoalkyl)acrylamide (see U.S. Pat. No. 3,878,247); or an acrylic or methacrylic acid ester can be reacted with an amine in gaseous phase in the presence of a solid acid catalyst such as vanadium-aluminum oxide at a temperature between 300° C. and 550° C. for a contact period of several seconds, to thereby produce the corresponding substituted acrylamide or methacrylamide (see U.S. Pat. No. 2,719,175). However, the first method involves several reaction steps and requires high operating temperatures, which leads to high energy costs, whereas the second method, which also uses high reaction temperatures, is accompanied by side reactions such as decomposition and polymerization, and the maximum yield of the product is only about 50%.

A method has recently been proposed to produce N-substituted acrylamide or methacrylamide by reacting an alkyl ester of acrylic or methacrylic acid with amine at from 50° C. to 180° C. in the presence of a catalytic amount of dialkyltin oxide (see U.S. Pat. No. 4,206,143). In this method, aminolysis of the ester group predominates over Michael addition to the carbon-carbon double bond, thereby producing the desired end product in a yield higher than was previously achieved. However, as described therein, even this method cannot produce the end compound without formation of a Michael addition product. As will be demonstrated in the Comparative Example herein, it has been confirmed by experiment that the method of U.S. Pat. No. 4,206,143 produces about 7 mol% of Michael addition products, one made up of the ester and amine, and the other made of the substituted amide and amine. When the reaction product is attempted to be refined by distillation, such Michael addition products are decomposed thermally and the amine is dissociated, thus failing to obtain an end product of high purity. It is therefore very desirable that the formation of Michael addition products in the reaction between alkyl ester of acrylic or methacrylic acid and amine be minimized.

SUMMARY OF THE INVENTION

Therefore, one object of this invention is to provide a process for producing N-substituted acrylamide or methacrylamide by reaction between an acrylic or methacrylic acid ester and amine which is characterized by producing the end product in high yield with minimum formation of Michael addition products and other impurities. Such object of this invention is achieved by using an alkyltin alkoxide as catalyst.

The process of this invention for producing N-substituted acrylamide or methacrylamide comprises reacting an acrylic or methacrylic acid ester with an aliphatic or aromatic amine in liquid medium in the presence of a catalytic amount of alkyltin alkoxide.

BRIEF DESCRIPTION OF THE DRAWING

The FIGURE is a graph showing the activity of the catalyst of this invention in terms of the relation between the reaction period (min.) and the temperature (°C.) at the upper part of a distillation column (hereinafter, the head temperature), which is indicative of the temperature of an azeotrope of methanol and methyl methacrylate obtained as a distillate.

In the FIGURE the solid line shows the result of Example 1, the broken line shows the result of Comparative Example 1, the one asterisk mark "*" shows the start of the addition of amine and the two asterisk marks "**" shows the completion of the addition of amine.

DETAILED DESCRIPTION OF THE INVENTION

As demonstrated by the Examples herein, the use of the alkyltin alkoxide catalyst specified in this invention remarkably inhibits the formation of Michael addition products and other by-products, and yet produces N-substituted acrylamide or methacrylamide in high yield and selectivity. As can be seen from the FIGURE, which represents one example of the reaction behavior in Examples in terms of the relation between the reaction period and the head temperature (i.e., the temperature at the upper part of a distillation column), which is indicative of the temperature of an azeotrope of methanol and methyl methacrylate obtained as a distillate, the conventional comparative method (indicated by the broken line) involves an induction period, whereas in the method of this invention (indicated by the solid line), an azeotrope of methanol and methyl methacrylate is obtained as distillate virtually immediately after the start of addition of amine, and its formation decreases more rapidly after the completion of addition of amine. This means that the alkyltin alkoxide according to this invention achieves a higher reaction rate and accelerates ester aminolysis more effectively than the conventional catalyst.

Examples of the alkyltin alkoxide suitable as catalyst in the process of this invention include butyltin trimethoxide, butyltin triethoxide, dibutyltin dimethoxide, dibutyltin diethoxide, dibutyltin diisoproxide, dibutyltin t-butoxide, dioctyltin dimethoxide, dioctyltin diethoxide, tributyltin methoxide, tributyltin ethoxide, triethyltin methoxide and trimethyltin methoxide.

The reactants necessary for the process of this invention are an acrylic or methacrylic acid ester and an aliphatic or aromatic amine. Combinations of aliphatic and aromatic amines may be used if desired. In the process of the present invention, the liquid or gaseous amine can be used at the room temperature under atmospheric pressure. Preferred examples of the acrylic or methacrylic acid ester are methyl acrylate and methyl methacrylate. Preferred examples of the aliphatic amine are an alkylamine of the formula $HNR^1R^2$ or $H_2NR^1$ (wherein $R^1$ and $R^2$ are each a straight or branched alkyl group having from 1 to 20 carbon atoms), an alkoxyalkylamine of the formula $H_2NR^3OR^4$ (wherein $R^3$ is an alkylene group having from 2 to 4 carbon atoms, and $R^4$ is an alkyl group having from 1 to 10 carbon atoms) and a polyamine of the formula $H_2NR^5N'R^6R^7$ (wherein $R^5$ is a straight or branched alkylene group having from 2 to 4 carbon atoms, $R^6$ and $R^7$ are each hydrogen or an alkyl group having from 1 to 6 carbon atoms, or when taken together with the N' atom, forms a heterocyclic ring selected from the group consisting of a morpholine ring, pyrrolidone ring, and piperidine ring). Specific examples include dimethylamine, butylamine, isoamylamine, n-octylamine, 2-methoxyethylamine, 2-methoxypropylamine, dimethylaminoethylamine, 3-dimethylaminopropylamine, 3-methylaminopropylamine, 3-diethylaminopropylamine, hexamethylenediamine, and cyclohexylaminopropylamine. Preferred examples of the aromatic amine are aniline and benzylamine.

Commercially available reactants as described above typically contain a slight moisture content. For example, commercially available methyl methacrylate usually has a moisture content of about 300 ppm or less, and commercially available dimethylaminopropylamine, usually has a moisture content of about 2,000 ppm or less, respectively. Such slight moisture content is permissible in the reaction of the present invention. According to a preferred embodiment of the process of the present invention, however, inactivation of the catalytic activity of alkyltin alkoxide can be prevented and the amount of alkyltin alkoxide required as a catalyst can be reduced by using reactants wherein the slight moisture content has been removed. Further, the yield of, and selectivity for, N-substituted acrylamide or methacrylamide is thereby increased. A zeolite is suitable for the dehydration of the above-described reactants. A zeolite preferably used is prepared by heating a hydrous metal salt of aluminosilicate of the formula $Me_{n/x}[(AlO_2)_x(SiO_2)_y]\cdot mH_2O$ (wherein the subscripts x, y, n and m represent atomic ratio, and when x is 1, y is 0.5 to 10, n is 0.5 to 2 and m is 1 to 10) until the water of crystallization is removed. Either natural or synthetic zeolite may be used. Zeolite having a pore size of from 3 to 5 Å, and particularly from 3 to 4 Å, is preferred. Examples of synthetic zeolite suitable in the process of this invention include Molecular Sieves (MS) 3A, 4A, 5A and XW types (manufactured by Union Carbide Co., Ltd.), Zeolon types, (manufactured by Norton Co., Ltd.), Neosorb ZB-3 (manufactured by Shokubai Kasei Co., Ltd.) and the like. Dehydration may be performed either by a batch or continuous process. The batch process is advantageously carried out by mixing the reactants with about 0.5 to about 50 wt% of zeolite on the basis of the reactants. The continuous process is advantageously carried out by supplying the reactants to a zeolite-packed column at a linear velocity in the column of from about 1 to 500 m/hr. Preferably the moisture content of the above described reactants should be low initially, e.g., the initial moisture content of the ester compounds and the amine compounds are preferably about 100 ppm or less and 200 ppm or less, respectively.

The reaction between the acrylic or methacrylic acid ester and amine is performed in liquid medium in the process of this invention. For example, the liquid or gaseous amine is added in the solution system wherein an alkyltin alkoxide is dissolved in an acrylic or methacrylic acid ester. Alcohol produced in the reaction is preferably removed from the reaction system as the reaction proceeds. The reaction may be started by mixing the ester, alkyltin alkoxide catalyst and amine together, but preferably, the amine or both ester and amine is added gradually to a liquid mixture of ester an alkyltin alkoxide catalyst. Alcohol produced in the reaction is preferably removed from the reaction system by a suitable distillation column at a suitable reflux ratio. The proportions of the reactants are such that 1 mol of amine is preferably reacted with at least 1 mol, and more preferably from about 1.5 to 4 mols, of ester. The alkyltin alkoxide is used typically in an amount of from about 0.05% to 10%, and preferably from about 0.1% to 3%, based on the weight of the amines. The reaction temperature is typically in the range of from about 40° C. to 200° C., and preferably from about 65° C. to 130° C. In the process of the present invention, since the reaction rate of the catalyst is high, the reaction can be completed even at the temperatures of 65° C. to 130° C. The reaction pressure is suitably from the atmospheric to subatmospheric. The reaction system preferably contains a polymerization inhibitor that prevents the polymerization the ester. Typical examples of inhibitor are phenothiazine and N-phenyl-2-naphthylamine.

The preferred embodiments of this invention and the resulting advantages are now described in greater detail by reference to examples and comparative examples, which are given here for illustrative purposes only, and are not intended to limit the scope of this invention.

EXAMPLE 1

A reactor (capacity=300 ml) with a stirrer and a distillation column 30 cm high that used hot water as a medium for heat exchange was supplied with 150.2 g of methyl methacrylate, 2 g of dibutyltin dimethoxide and 0.3 g of phenothiazine. While heating and stirring, 51.1 g of dimethylaminopropylamine was added gradually to the liquid mixture at 98° C. over a period of 90 minutes. Throughout the addition, nitrogen gas was supplied to the mixture and the water used as the heat exahanging medium was maintained at 80° C. After completion of the addition of amine, the reaction mixture was heated and stirred for another two hours, during which the resulting methanol was distilled off as an azeotrope with methyl methacrylate while the temperature of the mixture increased to 110° C. Then, the water used as heat exchanging medium was removed from the distillation column, whereupon the unreacted methyl methacrylate was distilled off. Then, the pressure in the reactor was gradually decreased and the unreacted reactants were distilled off sufficiently under reduced pressure. By the procedure described above, 87.5 g of the reaction mixture was obtained. Analysis of the reaction mixture by gas chromatography revealed that N-dimethylaminopropylmethacrylamide, a Michael addition product of methyl methacrylate, and a Michael addition product of N-dimethylaminopropylmethacrylamide were produced in yields of 98.1 mol%, 0.2 mol% and 0.6 mol%, respectively, on the basis of the dimethylaminopropylamine.

The FIGURE shows the relation between the reaction period and the head temperature indicative of the temperature of an azeotrope of methanol and methyl methacrylate obtained as distillate. From the FIGURE, it can be seen that the azeotrope of methanol and methyl methacrylate began to be obtained as distillate almost immediately after the start of the addition of amine (indicated by one asterisk) and its formation slowed down relatively soon after the completion of the addition of amine (indicated by two asterisks). It is therefore clear that the alkyltin alkoxide catalyst according to this invention achieves a high reaction rate.

COMPARATIVE EXAMPLE 1

The procedure of Example 1 was repeated, except that the catalyst was 2 g of dibutyltin oxide. The result was: N-dimethylaminopropylmethacrylamide, a Michael addition product of methyl methacrylate, and a Michael addition product of N-dimethylaminopropylmethacrylamide were formed in yields of 90.3 mol%, 4.5 mol% and 2.3 mol%, respectively, on the basis of dimethylaminopropylamine. The relation between the head temperature and reaction period for this example is depicted by the broken line in the FIGURE, from which it can be seen that the azeotrope of methanol and methyl methacrylate began to be obtained as distillate about 15 minutes after the start of the addition of amine and its formation continued at a relatively high level for an extend period of time after the completion of the addition. Thus it appears that the reaction that occurred in the process of this comparative example had an considerable induction period.

EXAMPLE 2

The procedure of Example 1 was repeated except that 53.6 g of benzylamine was used instead of dimethylaminopropylamine. The result was that N-benzylmethacrylamide was produced in a yield of 99 mol%, on the basis of the benzylamine.

EXAMPLE 3

A reactor of the type used in Example 1 was supplied with 200.2 g of methyl methacrylate, 2 g of dibutyltin dimethoxide and 0.4 g of phenothiazine. While stirring and heating, 18.3 g of gaseous dimethylamine was blown into the mixture at 95° C. over a period of 2 hours. Throughout the addition of dimethylamine, the mixture was stirred, and the temperature of the water used as the heat exchanging medium was kept at 80° C. After completion of the addition of dimethylamine, the reaction mixture was heated while stirring for 10 more minutes before it was cooled. Analysis of the reaction mixture by gas chromatography showed that N,N-dimethylmethacrylamide, a Michael addition product of methyl methacrylate, and other by-products were formed in selectivities of 98.9%, 0.7% and 0.4%, respectively.

COMPARATIVE EXAMPLE 2

The procedure of Example 3 was repeated, except that catalyst was dibutyltin oxide. The result was: N,N-dimethylmethacrylamide and methyl methacrylate were obtained in selectivities of 93.0% and 7.0%, respectively.

EXAMPLE 4

A reactor (capacity = 3,000 ml) equipped with a stirrer and a distillation column having 10 trays of perforated plates was fed with a mixture 1,502 g of methyl methacrylate, 22 g of dibutyltin diethoxide and 3 g of phenothiazine. The liquid mixture was heated in an oil bath (140° C.) while stirring. When the mixture boiled, 511 g of 3-dimethylaminopropylamine was gradually added to the mixture over a period of 3 hours during which an azeotrope of methyl methacrylate and methanol was distilled off at a head temperature of from 65° C. to 75° C. which was maintained by suitable control of the reflux ratio (the ratio of the distillate solution and the refluxing solution). After completion of the addition of 3-dimethylaminopropylamine, the mixture was heated at the temperature 113° C. while stirring for another hour. The temperature of the reaction mixture per se was 113° C. The resulting reaction mixture was analyzed by gas chromatography: N-dimethylaminopropylmethacrylamide, a Michael addition product of methyl methacrylate, and a Michael addition product of N-dimethylaminopropylmethacrylamide were produced in yields of 98.5 mol%, 1.0 mol%, and 0.2 mol%, respectively, on the basis of 3-dimethylaminopropylamine.

EXAMPLE 5

The procedure of Example 4 was repeated, except that the catalyst was 25 g of dibutyltin diisopropoxide and that the mixture was heated under stirring for two more hours after completion of the addition of amine. N-Dimethylaminopropylmethacrylamide, a Michael addition product of methyl methacrylate, and a Michael addition product of N-dimethylaminopropylmethacrylamide were produced in yields of 97.1 mol%, 2.1 mol% and 0.3 mol%, respectively.

EXAMPLE 6

The procedure of Example 5 was repeated, except that the catalyst was 27 g of tributyltin ethoxide. N-dimethylaminopropylmethacrylamide, a Michael addition product of methyl methacrylate, and a Michael addition product of N-dimethylaminopropylmethacrylamide were produced in yields of 96.5 mol%, 2.2 mol%, and 0.5 mol%, respectively.

EXAMPLE 7

A glass column packed with 100 g of a molecular sieve 4A bed (the particle size: 8-12 mesh, 50 cm high) was supplied from overhead with methyl methacrylate at a linear velocity in column of 30 m/hr. The initial water content of 300 ppm was reduced to 30 ppm by this dehydration treatment. When 3-dimethylaminopropylamine was treated in the same manner, the water content was reduced from 2,000 ppm to 150 ppm.

A 300 ml-capacity reactor with a distillation column and a stirrer was purged with nitrogen gas and supplied with 150.2 g of the dehydrated methyl methacrylate, 1.4 g of dibutyltin dimethoxide and 0.2 g of phenothiazine. The liquid mixture was heated in an oil bath (135° C.) under stirring. Then, 51.1 g of the dehydrated 3-dimethylaminopropylamine was added gradually to the mixture at 100° C. over a period of 3 hours. Throughout the addition period, the head temperature was held at from 65° C. to 70° C. by control of the reflux ratio (the ratio of the distillate solution and the refluxing solution). After completion of the addition of amine, the reaction mixture was heated under stirring for another 1.5 hours, during which the resulting methanol was distilled off as an azeotrope with methyl methacrylate. The temperature of the reaction solution per se was 114° C. Excess methyl methacrylate was distilled off at a head temperature of from 65° C. to 70° C. which was maintained by suitable control of the reflux ratio (the ratio of the distillate solution and the refluxing solution), and the pressure in the reactor was reduced until the low-boiling components were distilled off. A crude product was obtained in an amount of 86.8 g. Analysis of the crude product by gas chromatography showed that N-dimethylaminopropylmethacrylamide and a Michael addition product of methyl methacrylate were produced in yields of 99.0 mol% and 0.5 mol%, respectively, on the basis of 3-dimethylaminopropylamine, with only a trace of a Michael addition product of N-dimethylaminopropylmethacrylamide being formed.

EXAMPLE 8

Methyl methacrylate and benzylamine were dehydrated as in Example 7. The subsequent procedure was the same as in Example 7, except for the following points: 200.2 g of dehydrated methyl methacrylate and 53.6 g of dehydrated benzylamine (instead of 3-dimethylaminopropylamine) were used; the amine was added to the mixture over a period of 2 hours; and the aging period after addition of amine was 2 hours. Upon cooling of the reaction mixture, white crystals were formed. Analysis of the reaction mixture by gas chromatography showed that the percent conversion of benzylamine was almost 100% and the selectivity for N-benzylmethacrylamide was more than 99.9%, with the formation of by-products being negligible. The crystalline product was filtered, dried with hot air at 60° C., and subjected to IR and NMR analyses which confirmed that the product was N-benzylmethacrylamide.

While the invention has been described in detail and with reference to specific embodiments thereof, it will be apparent to one skilled in the art that various changes and modifications can be made therein without departing from the spirit and scope thereof.

What is claimed is:

1. A process for producing N-substituted acrylamide or methacrylamide comprising reacting an acrylic or methacrylic acid ester with aliphatic and/or aromatic amine in liquid medium in the presence of a catalytic amount of alkyltin alkoxide.

2. A process according to claim 1 wherein the acrylic or methacrylic acid ester and the aliphatic or aromatic amine are dehydrated.

3. A process according to claim 1 or 2 wherein the alkyltin alkoxide is dibutyltin dimethoxide, dibutyltin diethoxide, dibutyltin diisopropoxide, or tributyltin ethoxide.

4. A process according to claim 1 or 2 wherein the alkyltin alkoxide is used in an amount of from 0.05% to 10% based on the weight of the amines.

5. A process according to claim 4 wherein the alkyltin alkoxide is used in an amount of from 0.1 % to 3%.

6. A process according to claim 3 wherein the alkyltin alkoxide is used in an amount of from 0.05% to 10% based on the weight of the amines.

7. A process according to claim 6 wherein the alkyltin alkoxide is used in an amount of from 0.1% to 3%.

8. A process according to claim 2 wherein the dehydrating means is zeolite.

9. A process according to claim 8 wherein the zeolite has a pore size of from 3 Å to 5 Å.

10. A process according to claim 1 wherein the reaction is carried out at the temperature of from 40° C. to 200° C.

11. A process according to claim 10 wherein the reaction is from 65° C. to 130° C.

* * * * *